United States Patent
Ignatyev et al.

(10) Patent No.: US 7,550,491 B2
(45) Date of Patent: Jun. 23, 2009

(54) IONIC LIQUIDS HAVING [N(CF$_3$)$_2$]$^-$ ANIONS

(75) Inventors: Nikolai Ignatyev, Duisburg (DE); Urs Welz-Biermann, Heppenheim (DE); Michale Schmidt, Seeheim-Jugenheim (DE); Helge Willner, Mühlheim/Ruhr (DE); Andriy Kucheryna, Duisburg (DE)

(73) Assignee: Merck Patent GmbH, Darmstadt (DE)

( * ) Notice: Subject to any disclaimer, the term of this patent is extended or adjusted under 35 U.S.C. 154(b) by 517 days.

(21) Appl. No.: 10/538,847

(22) PCT Filed: Nov. 17, 2003

(86) PCT No.: PCT/EP03/21811

§ 371 (c)(1),
(2), (4) Date: Jun. 13, 2005

(87) PCT Pub. No.: WO2004/054991

PCT Pub. Date: Jul. 1, 2004

(65) Prior Publication Data

US 2006/0079691 A1    Apr. 13, 2006

(30) Foreign Application Priority Data

Dec. 13, 2002   (DE) ................................. 102 58 671

(51) Int. Cl.
*C07D 213/18* (2006.01)
*A61K 31/44* (2006.01)
(52) U.S. Cl. .................... 514/358; 514/365; 514/396; 514/427; 546/347; 548/146; 548/300.1; 548/400
(58) Field of Classification Search ...................... None
See application file for complete search history.

(56) References Cited

U.S. PATENT DOCUMENTS 5,827,602 A    10/1998   Nanjundiah et al.
6,582,849 B1    6/2003   Heider et al.

FOREIGN PATENT DOCUMENTS

EP        1 081 129       3/2001
WO    WO 02/064542      8/2002

OTHER PUBLICATIONS

Sheldon R: "Catalytic Reactions in Ionic Liquids" Chemical Communications—Chemcom, Royal Society of Chemistry, GB, Nr. 23, Oct. 18, 2001, Seiten 2399-2407.

*Primary Examiner*—Zinna N Davis
(74) *Attorney, Agent, or Firm*—Miller, White, Zelano, Branigan, P.C.

(57) ABSTRACT

The present invention relates to salts comprising bis(trifluoromethyl)imide anions and saturated, partially or fully unsaturated, heterocyclic cations, to a process for the preparation thereof, and to the use thereof as ionic liquids.

28 Claims, No Drawings

IONIC LIQUIDS HAVING [N(CF$_3$)$_2$]$^-$ ANIONS

The present invention relates to salts comprising bis(trifluoromethyl)imide anions and saturated, partially or fully unsaturated, heterocyclic cations, to a process for the preparation thereof, and to the use thereof as ionic liquids.

Ionic liquids or liquid salts are ionic species which consist of an organic cation and a generally inorganic anion. They do not contain any neutral molecules and have melting points of below 373 K. A multiplicity of compounds which are used as ionic liquids are known in the prior art. In particular, they are also the subject-matter of a series of patents and patent applications.

Thus, solvent-free ionic liquids were disclosed for the first time by Hurley and Wier in a series of U.S. patents (U.S. Pat. Nos. 2,446,331, 2,446,339 and 2,446,350). These "salts which are molten at room temperature" comprised AlCl$_3$ and a multiplicity of n-alkylpyridinium halides.

U.S. Pat. No. 5,827,602 describes hydrophobic ionic liquids having a wide electrochemical window for use as electrolytes in batteries. These salts have certain 5- or 6-membered heterocyclic cations and polyatomic anions having a van der Waals radius of greater than 100 Å$^3$, for example halogenated alkylsulfonimides, mono- or diperfluorosulfonates, fluorinated alkylfluorophosphates.

In addition, some review articles on this topic have been published in recent years (R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionische Flüssigkeiten—neue Lösungen für die Übergangsmetallkatalyse" [Ionic Liquids—Novel Solutions for Transition-Metal Catalysis], *Angew. Chem.*, 112 (2000), 3926-3945; T. Welton "Room temperature ionic liquids. Solvents for synthesis and catalysis", *Chem. Rev.*, 92 (1999), 2071-2083; R. Hagiwara, Ya. Ito "Room temperature ionic liquids of alkylimidazolium cations and fluoroanions", *Journal of Fluorine Chem.*, 105 (2000), 221-227).

EP 1 081 129 discloses stable N(CF$_3$)$_2^-$ salts having tetraalkylammonium and comparable cations. Neither heterocyclic cations nor use of the disclosed compounds as ionic liquids are described.

The properties of ionic liquids, for example melting point, thermal and electro-chemical stability, viscosity, are greatly influenced by the nature of the anion. By contrast, the polarity and hydrophilicity or lipophilicity can be varied through a suitable choice of the cation/anion pair. There is therefore a demand for novel ionic liquids having varied properties which facilitate additional possibilities regarding their use.

The object of the present invention is to provide novel stable compounds having valuable properties which can be used as ionic liquids, and a process for the preparation thereof.

This object is achieved by the provision of salts of the general formula (1)

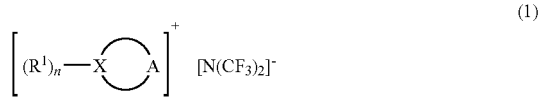 (1)

which have a bis(trifluoromethyl)imide anion and a saturated, partially or fully unsaturated, heterocyclic cation.

In this formula:
X denotes N, P, O or S
n denotes an integer selected from 0, 1 or 2 in such a way that
  X is saturated in accordance with its valency increased by 1,
A denotes a saturated, partially or fully unsaturated 3- to 8-membered hydrocarbon chain,
  in which all carbon atoms apart from one may be replaced by identical or different heteroatoms, selected from N, P, O and S,
  where the carbon atoms of the hydrocarbon chain and the heteroatoms present therein are saturated by substituents R$^2$ in accordance with their valency,
R$^1$, R$^2$ denote —H, with the proviso that there is no bond to the positively charged heteroatom,
  straight-chain or branched alkyl having 1-20 carbon atoms
  straight-chain or branched alkenyl having 2-20 carbon atoms and one or more double bonds
  straight-chain or branched alkynyl having 2-20 carbon atoms and one or more triple bonds
  saturated, partially or fully unsaturated cycloalkyl having 3-7 carbon atoms
  halogen, in particular fluorine or chlorine, with the proviso that, for X=N, O, S, there is no halogen-heteroatom bond,
  —NO$_2$, with the proviso that there is no bond to the positively charged heteroatom,
  —CN, with the proviso that there is no bond to the positively charged heteroatom,
  where the R$^2$ and/or R$^1$ in different and/or identical position of the heterocyclic ring are in each case identical or different,
  where the R$^2$ and/or R$^1$ may be connected to one another in pairs by a single or double bond,
  where one or more R$^2$ and/or R$^1$ may be partially or fully substituted by halogens, in particular —F and/or —Cl, or partially by —CN or —NO$_2$, with the proviso that not all R$^2$ and R$^1$ are fully halogenated,
  and where one or two carbon atoms of the R$^1$ and/or R$^2$ may be replaced by heteroatoms and/or atomic groups selected from the group —O—, —C(O)—, C(O)O—, —S—, —S(O)—, —SO$_2$—, —SO$_2$O—, —N=, —P=, —NH—, —PH—, —NR'— and —PR'— where R'=non-, partially or perfluorinated C$_1$- to C$_6$-alkyl or —C$_6$F$_5$, where the α-position of the R$^1$ is not replaced for X=O, S.

For the purposes of the present invention, the valency of the atom is taken to mean the number of bonds which emanate from a neutral atom or the number of electron pairs that a neutral atom shares with other atoms in a molecule and which are represented as valence dashes in the simplified representation of the electron formulae. In accordance with the invention, nitrogen and phosphorus atoms therefore have a valency of 3, oxygen and sulfur atoms a valency of 2 and carbon atoms a valency of 4. Phosphorus atoms may, if they are neutral atoms of the cation, also have a valency of 5.

For the purposes of the present invention, fully unsaturated compounds or substituents are also taken to mean aromatic compounds or aromatic substituents.

The compounds according to the invention are salts which have an N(CF$_3$)$_2^-$ anion and, as cation, a heterocyclic 4- to 9-membered ring, which is saturated or unsaturated. Suitable heteroatoms here are N, P, O or S. Besides the heteroatom carrying the positive charge, the heterocyclic ring may also contain further, identical or different heteroatoms selected from the group N, P, O and S; however, the ring contains at least one carbon atom.

Suitable cations according to the invention are heterocyclic compounds which are stable, in particular which can be isolated.

All atoms of the heterocyclic ring each carry so many identical or different substituents R$^1$ or R$^2$ that they are saturated in accordance with their valency. In the case of the positively charged heteroatom, the number of substituents corresponds to the valency increased by 1.

Some examples are given below which are intended to document the number of substituents per ring atom in accordance with the invention: monounsaturated or aromatic, i.e. sp²-hybridised, carbon atoms have one substituent, while saturated sp³-hybridised carbon atoms have two substituents. An oxygen or sulfur atom carrying a positive charge which is bonded into the cyclic ring by means of a double bond has no substituents, just like an oxygen or sulfur atom with no positive charge which is singly bonded into the cyclic ring and a nitrogen or phosphorus atom with no positive charge which is bonded into the cyclic ring by means of a double bond. Oxygen or sulfur atoms having a positive charge which are singly bonded into the cyclic ring and nitrogen or phosphorus atoms having a positive charge which are bonded into the cyclic ring by means of a double bond and nitrogen or phosphorus atoms with no positive charge which are singly bonded into the cyclic ring carry one substituent.

Besides hydrogen, suitable substituents $R^1$, $R^2$ of the heterocyclic ring are, in accordance with the invention: $C_1$- to $C_{20}$—, in particular $C_1$- to $C_{12}$-alkyl groups, $C_2$- to $C_{20}$-, in particular $C_2$- to $C_{12}$-, alkenyl or alkynyl groups, saturated or unsaturated, i.e. also aromatic, $C_3$- to $C_7$-cycloalkyl groups, $NO_2$, CN or halogens. For the halogens, however, a restriction is that they only occur as substituents on carbon atoms or on phosphorus atoms of the heterocyclic ring, but not on the heteroatoms N, O, S. H, $NO_2$ and CN do not occur as substituents of the positively charged heteroatom.

The substituents $R^1$, $R^2$ may also be connected in pairs in such a way that bi- or polycyclic cations arise. The substituents may be partially or fully substituted by halogen atoms, in particular by F and/or Cl, or partially by CN or $NO_2$ and contain one or two heteroatoms or atomic groups selected from the group O, C(O), C(O)O, S, S(O), $SO_2$, $SO_2O$, N, P, NH, PH, NR', PR'. In the case of full halogenation, however, not all substituents $R^1$ and $R^2$ present may be fully halogenated, i.e. at least one $R^1$ and/or $R^2$ is not perhalogenated.

Without restricting generality, examples of substituents according to the invention of the heterocyclic cation are:

—F, —Cl, —Br, —I, —$CH_3$, —$C_2H_5$, —$C_3H_7$, —CH($CH_3$)$_2$, —$C_4H_9$, —C($CH_3$)$_3$, —$C_5H_{11}$, —$C_6H_{13}$, —$C_6H_{13}$, —$C_7H_{15}$, —$C_8H_{17}$, —$C_9H_{19}$, —$C_{10}H_{21}$, —$C_{12}H_{25}$, —$C_{20}H_{41}$, —$OCH_3$, —$OCH(CH_3)_2$, —$CH_2OCH_3$, —$C_2H_4OCH(CH_3)_2$, —$SCH_3$, —SCH($CH_3$)$_2$, —$C_2H_4SC_2H_5$, —$C_2H_4SCH(CH_3)_2$, —S(O)$CH_3$, —$SO_2CH_3$, —$SO_2C_2H_5$, —$SO_2C_3H_7$, —$SO_2CH(CH_3)_2$, —$CH_2SO_2CH_3$, —$OSO_2CH_3$, —$OSO_2CF_3$, —$CH_2N(H)$ $C_2H_5$, —$C_2H_4N(H)C_2H_5$, —$CH_2N(CH_3)CH_3$, —$C_2H_4N$ ($CH_3$)$CH_3$, —$N(CH_3)_2$, —$N(CH_3)C_3H_5$, —$N(CH_3)CF_3$, O—$C_4H_8$—O—$C_4H_9$, —S—$C_2H_4$—$N(C_4H_9)_2$, —$OCF_3$, —S(O)$CF_3$, —$SO_2CF_3$, —$CF_3$, —$C_2F_5$, —$C_3F_7$, —$C_4F_9$, —C($CF_3$)$_3$, —$CF_2SO_2CF_3$, —$C_2F_4N(C_2F_5)C_2F_5$, —CF=$CF_2$, —C($CF_3$)=$CFCF_3$, —$CF_2CF$=$CFCF_3$, —CF=$CFN(CF_3)CF_3$, —$CFH_2$, —$CHF_2$, —$CH_2CF_3$, —$C_2F_2H_3$, —$C_3H_6$, —$CH_2C_3F_7$, —C($CFH_2$)$_3$, —CHO, —C(O)OH, —$CH_2C(O)OH$, —$CH_2C(O)CH_3$, —$CH_2C$(O)$C_2H_5$, —$CH_2C(O)OCH_3$, $CH_2C(O)OC_2H_5$, —C(O)$CH_3$, —C(O)O$CH_3$,

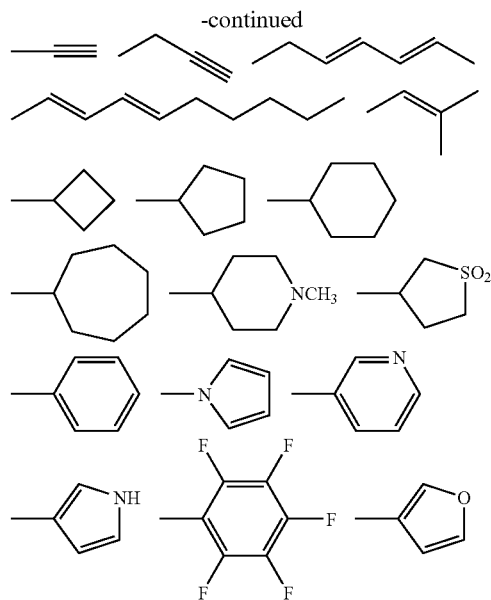

According to model calculations, the [N(CF$_3$)$_2$]⁻ anion has a van der Waals radius of 90.90 Å³ and is thus relatively small compared with the ionic liquid anions known from the prior art.

The salts according to the invention are not hydrophobic, i.e. they are at least to a certain extent miscible with water.

In addition, the salts according to the invention are advantageously very highly soluble in organic solvents.

Compared with known liquid salts, the salts according to the invention surprisingly have low viscosity.

Advantageously, the salts according to the invention are stable. They can be isolated and stored at room temperature.

Furthermore, the salts according to the invention are relatively simple to prepare, while, in particular, the [N(SO$_2$CF$_3$)$_2$]⁻ anion known from the prior art is only accessible with difficulty and in particular is very expensive.

In salts which are preferred in accordance with the invention, the cation has a heterocyclic, saturated or unsaturated five-, six- or seven-membered ring. An example of a five-membered ring according to the invention having only one carbon atom is the tetrazolium cation, for example in

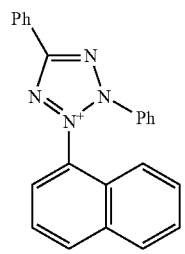

In a further preferred variant of the salts according to the invention, the heterocyclic ring of the cation contains a total of at most 3 heteroatoms selected from N, P, O or S. In the case of a plurality of heteroatoms, it is very particularly preferred for only a maximum of 2 heteroatoms to be arranged directly adjacent.

Besides hydrogen atoms, preferred substituents for the heterocyclic ring are halogens, in particular fluorine, so long as these are not bonded to a heteroatom with the exception of phosphorus, straight-chain or branched $C_1$- to $C_6$-alkyl groups, in particular —$CH_3$, —$C_2H_5$, -n-$C_3H_7$, —$CH(CH_3)_2$, -n-$C_4H_9$, -n-$C_6H_{13}$ and straight-chain or branched, partially or perfluorinated $C_1$- to $C_6$-alkyl groups, in particular —$CF_3$, —$C_2F_5$, —$C_4F_9$.

A preferred embodiment of the invention are salts in which the saturated, partially or fully unsaturated heterocyclic cation is a five- or six-membered ring having the following structure:

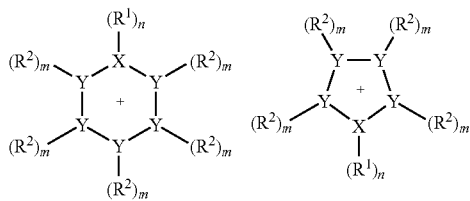

where X is selected from the group N, P, O and S and Y is in each case, independently of one another, selected from the group C, N, P, O and S, where at least one Y is a carbon atom, while the remaining three or four Y can be carbon or heteroatoms.

The number n of substituents $R^1$ on the positively charged heteroatom X corresponds to the valency increased by 1, i.e. unsaturated oxygen or sulfur atoms have no substituents, saturated oxygen and sulfur atoms, like unsaturated nitrogen and phosphorus atoms, have one substituent $R^1$ and saturated nitrogen and phosphorus atoms have two substituents $R^1$.

The remaining atoms (Y) of the heterocyclic ring each have so many (m) identical or different substituents $R^2$ that they are saturated in accordance with their valency, i.e. saturated oxygen and sulfur atoms, like unsaturated nitrogen and phosphorus atoms, have no substituents, saturated nitrogen and phosphorus atoms as well as unsaturated, sp$^2$-hybridised carbon atoms have one substituent $R^2$ and saturated, sp$^3$-hybridised carbon atoms have two substituents $R^2$.

The substituents $R^1$ and $R^2$ are defined as in the general formula (1).

In this embodiment, particular preference is given to the variants in which the heteroatoms of the saturated or unsaturated five- or six-membered ring of the cation are distributed in such a way that the cation is selected from the following group:

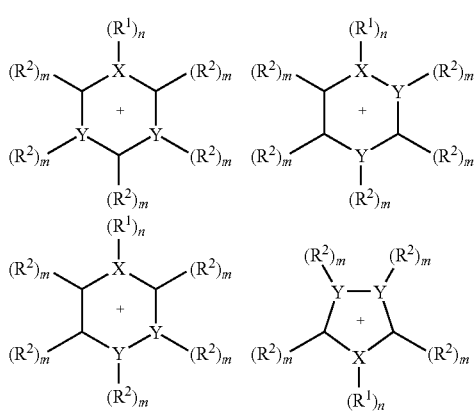

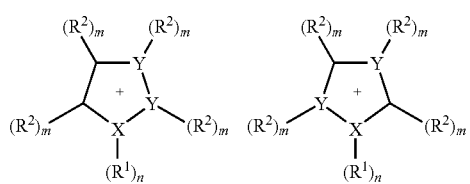

where X selected from the group N, P, O and S and Y in each case, independently of one another, selected from the group C, N, P, O and S. The number n, m of substituents $R^1$, $R^2$ on the positively charged heteroatom X or the remaining atoms of the heterocyclic ring are defined in accordance with the general formulae for the five- or six-membered ring cations. The substituents $R^1$ and $R^2$ are defined as in the general formula (1).

Without restricting generality, examples of such cations according to the invention having a five- or six-membered ring are:

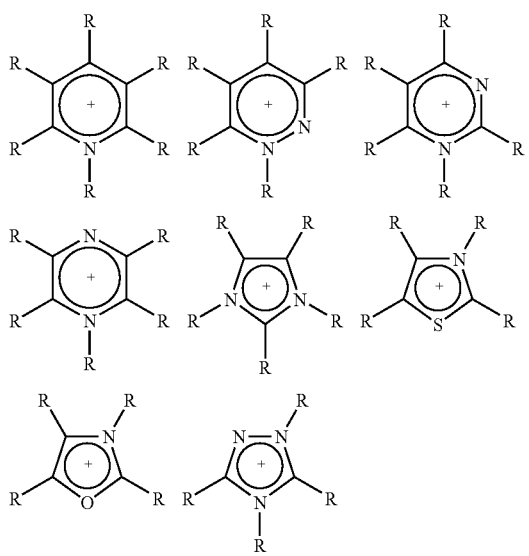

where the substituents R are defined, independently of one another, like $R^1$ and $R^2$ in the general formula (1), and also

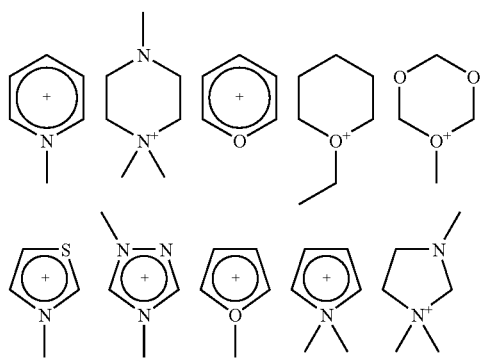

-continued

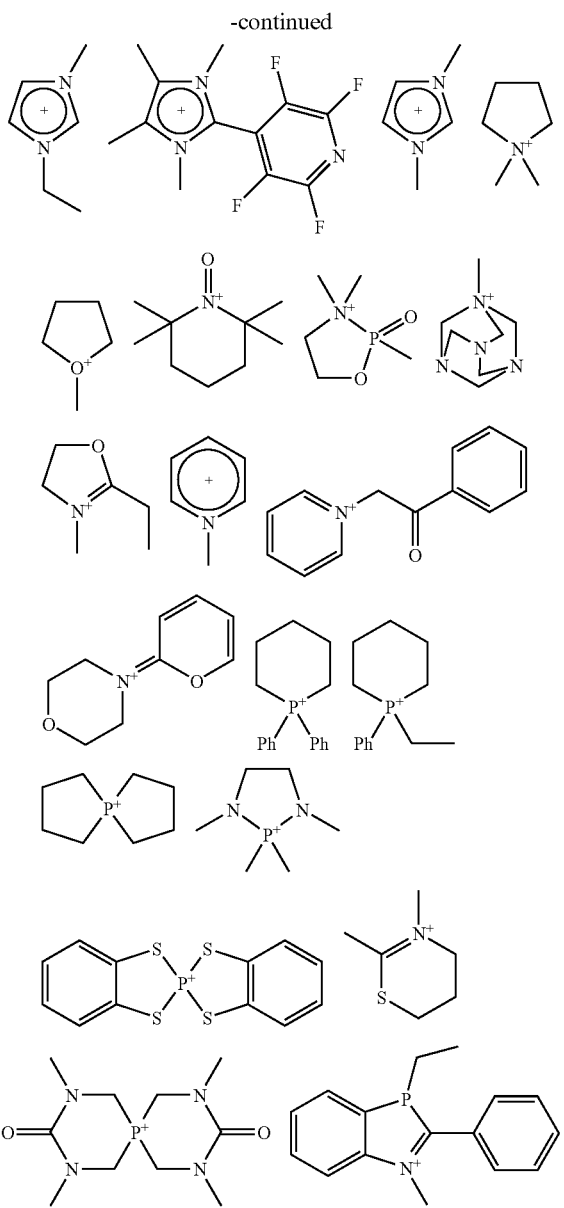

In a further preferred variant, salts according to the invention have a saturated, partially or fully unsaturated, heterocyclic cation which contains a fused ring, i.e. a cation in which two adjacent substituents of the heterocyclic ring are connected to one another, and which is selected from the following group:

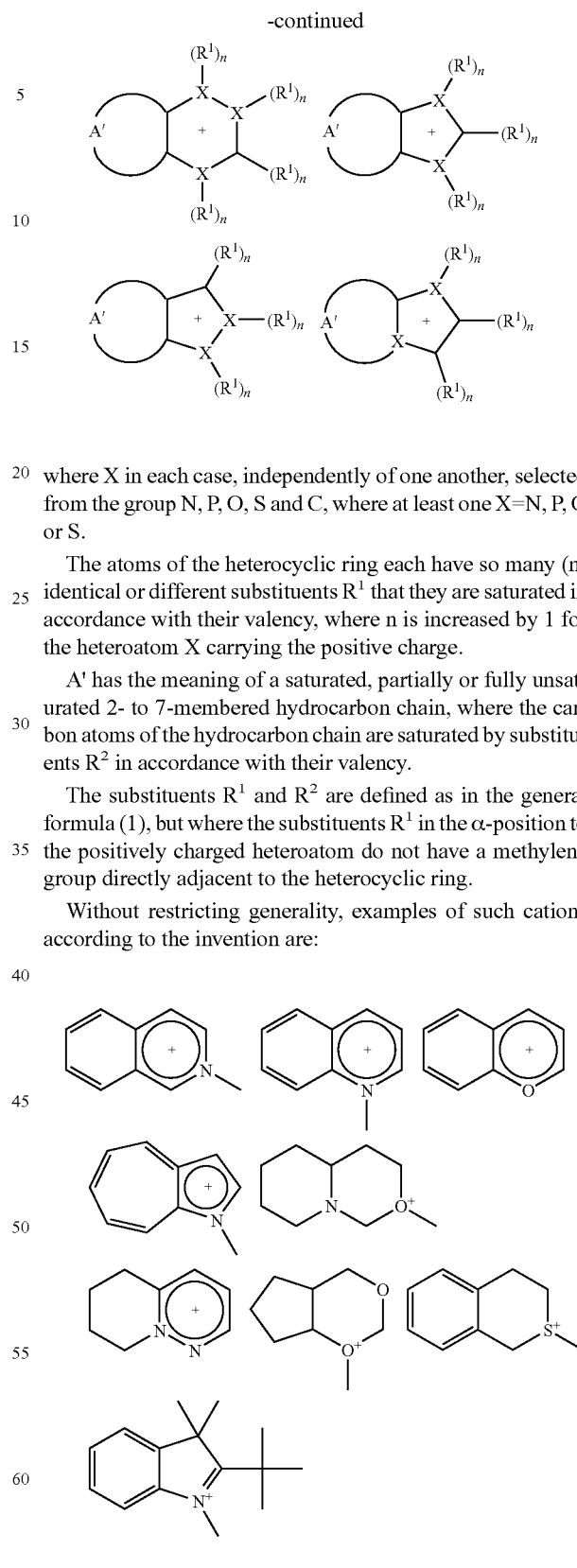

where X in each case, independently of one another, selected from the group N, P, O, S and C, where at least one X=N, P, O or S.

The atoms of the heterocyclic ring each have so many (n) identical or different substituents $R^1$ that they are saturated in accordance with their valency, where n is increased by 1 for the heteroatom X carrying the positive charge.

A' has the meaning of a saturated, partially or fully unsaturated 2- to 7-membered hydrocarbon chain, where the carbon atoms of the hydrocarbon chain are saturated by substituents $R^2$ in accordance with their valency.

The substituents $R^1$ and $R^2$ are defined as in the general formula (1), but where the substituents $R^1$ in the α-position to the positively charged heteroatom do not have a methylene group directly adjacent to the heterocyclic ring.

Without restricting generality, examples of such cations according to the invention are:

Preference is furthermore given to salts according to the invention in which the saturated, partially or fully unsaturated heterocyclic cation has the following structure:

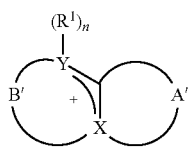

where X selected from the group N and P and Y selected from the group N, P, O and S.

The number n of substituents $R^1$ on the heteroatom Y is 0 in the case of an oxygen or sulfur atom and is 1 in the case of a nitrogen or phosphorus atom.

A' has the meaning of a 2- to 7-membered, B' that of a 1- to 6-membered hydrocarbon chain, where the hydrocarbon chains are saturated, partially or fully unsaturated and in which all carbon atoms apart from one may be replaced by identical or different heteroatoms selected from N, P, O and S and where the carbon atoms of the hydrocarbon chains A' and B' are saturated by substituents $R^2$ in accordance with their valency.

The substituents $R^1$ and $R^2$ are defined as in the general formula (1).

Without restricting generality, examples of such cations according to the invention are:

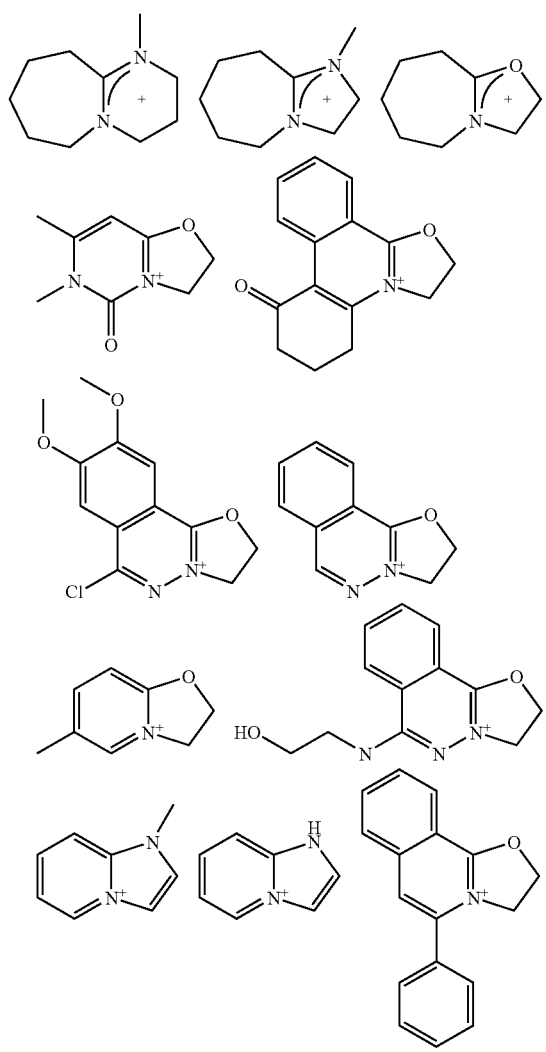

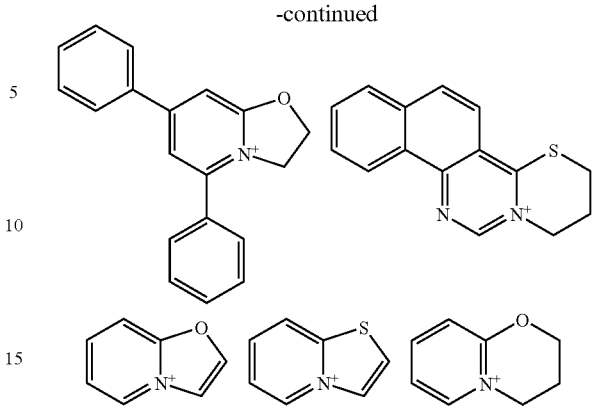

The present invention relates secondly to salts of the general formula (2)

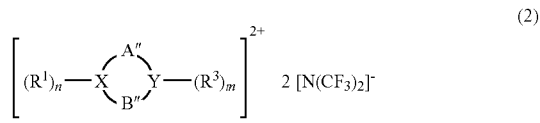

which contain a bis(trifluoromethyl)imide anion and a saturated or unsaturated, heterocyclic di-cation, i.e. a heterocyclic 4- to 9-membered ring which is saturated or unsaturated and contains two positively charged heteroatoms.

In this formula:

X, Y each, independently of one another, denote N, P, O or S n, m denote an integer selected from 0, 1 or 2 in such a way that X, Y are each saturated in accordance with their valency increased by 1, A", B" denote saturated, partially or fully unsaturated 0- to 4-membered hydrocarbon chain,
  in which the carbon atoms may be replaced by identical or different heteroatoms selected from N, P, O and S,
  where at least one carbon atom is present in the chains A" and B" together and
  where the carbon atoms of the hydrocarbon chains A" and B" and the heteroatoms present therein are saturated by substituents $R^2$ in accordance with their valency, $R^1$, $R^2$, $R^3$ denote —H, with the proviso that there is no bond to the positively charged heteroatom,
  straight-chain or branched alkyl having 1-20 carbon atoms
  straight-chain or branched alkenyl having 2-20 carbon atoms and one or more double bonds
  straight-chain or branched alkynyl having 2-20 carbon atoms and one or more triple bonds
  saturated, partially or fully unsaturated cycloalkyl having 3-7 carbon atoms
  halogen, in particular fluorine or chlorine, with the proviso that, for X=N, O, S, there is no halogen-heteroatom bond,
  —$NO_2$, with the proviso that there is no bond to a positively charged heteroatom,
  —CN, with the proviso that there is no bond to a positively charged heteroatom,
  where the $R^1$, $R^2$ and/or $R^3$ in different and/or identical position of the heterocyclic ring are in each case identical or different, where the $R^1$, $R^2$ and/or $R^3$ may be connected to one another in pairs by a single or double bond, where one or more $R^1$, $R^2$ and/or $R^3$ may be partially or fully substituted by halogens, in particular —F and/or —Cl, or partially by —CN or —NO$_2$, with the proviso that not all $R^1$, $R^2$ and $R^3$ are fully halogenated, and where one or two carbon atoms of the $R^1$, $R^2$ and/or $R^3$ may be replaced by heteroatoms and/or atomic groups selected from the group —O—, —C(O)—, C(O)O—, —S—, —S(O)—, —SO$_2$—, —SO$_2$O—, —N=, —P=, —NH—, —PH—, —NR'— and —PR'— where R'= non-, partially or perfluorinated C$_1$- to C$_6$-alkyl or —C$_6$F$_5$, where the α-positions of the $R^1$ and of the $R^3$ are not replaced for X=O, S or Y=O, S, where the heterocyclic di-cation is a 4-, 5-, 6-, 7-, 8- or 9-membered ring.

In preferred salts, the di-cation has a heterocyclic, saturated or unsaturated five-, six- or seven-membered ring.

Without restricting generality, examples of such di-cations according to the invention are:

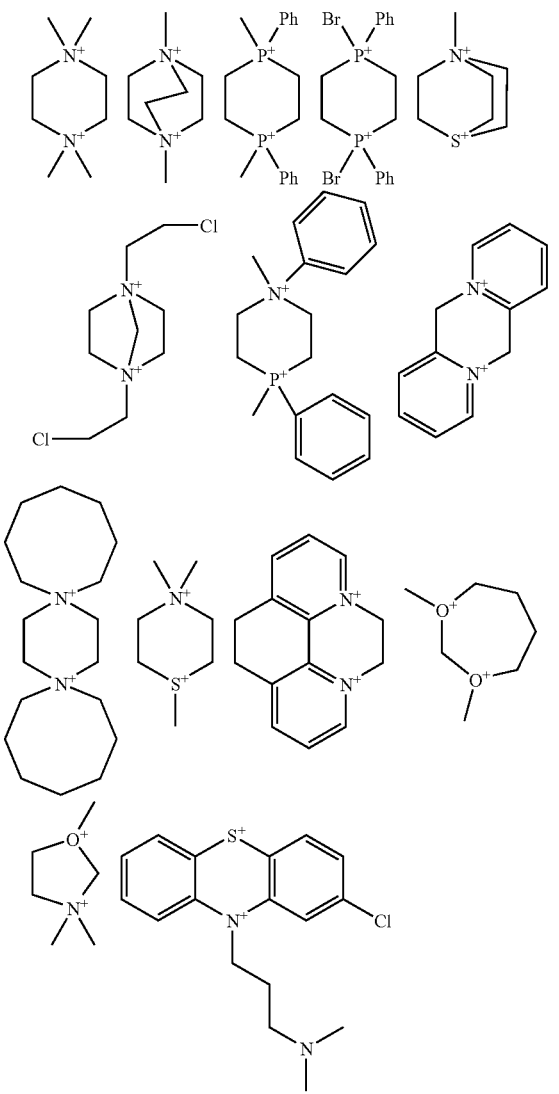

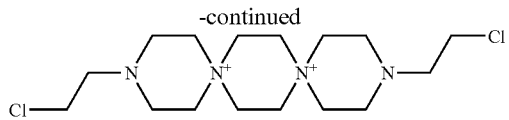

The present invention furthermore relates to salts of the general formula (3)

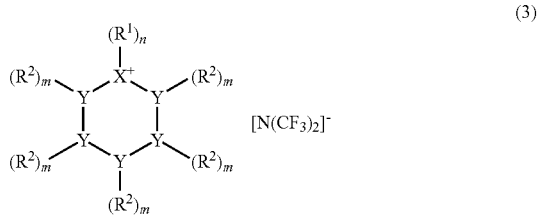

which contain a bis(trifluoromethyl)imide anion and a saturated partially or fully unsaturated, heterocyclic cation whose heterocyclic six-membered ring contains no carbon atoms.

In this formula:

X, Y each, independently of one another, denote N, P, O or S n denotes an integer selected from 0, 1 or 2 in such a way that X is saturated in accordance with its valency increased by 1, m denotes an integer selected from 0, 1 or 2 in such a way that Y is saturated in accordance with its valency, $R^1$, $R^2$ denote —H, with the proviso that there is no bond to the positively charged heteroatom, straight-chain or branched alkyl having 1-20 carbon atoms straight-chain or branched alkenyl having 2-20 carbon atoms and one or more double bonds straight-chain or branched alkynyl having 2-20 carbon atoms and one or more triple bonds saturated, partially or fully unsaturated cycloalkyl having 3-7 carbon atoms halogen, in particular fluorine or chlorine, with the proviso that, for X=N, O, S, there is no halogen-heteroatom bond, —OR, with the proviso that the substituted heteroatom is not O or S, where the $R^2$ and/or $R^1$ in different and/or identical position of the heterocyclic ring are in each case identical or different, where the $R^2$ and/or $R^1$ may be connected to one another in pairs by a single or double bond, where one or more $R^2$ and/or $R^1$ may be partially or fully substituted by halogens, in particular —F and/or —Cl, or partially by —CN or —NO$_2$, with the proviso that not all $R^2$ and $R^1$ are fully halogenated, and where one or two carbon atoms of the $R^1$ and/or $R^2$ may be replaced by heteroatoms and/or atomic groups selected from the group —O—, —C(O)—, C(O)O—, —S—, —S(O)—, —SO$_2$—, —SO$_2$O—, —N=, —P=, —NH—, —PH—, —NR'— and —PR'— where R'= non-, partially or perfluorinated C$_1$- to C$_6$-alkyl or —C$_6$F$_5$, where the α-position of the $R^1$ is not replaced for X=O, S.

Without restricting generality, examples of such cations according to the invention are:

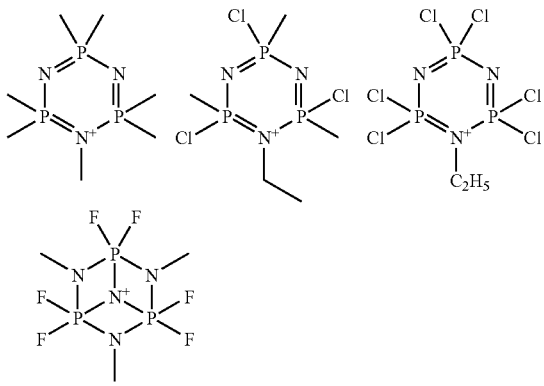

It has been found that the compounds according to the invention can easily be synthesised under mild conditions. The salts according to the invention are isolated with high yields.

To this end, compounds of the general formula

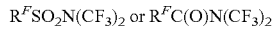

$R^F SO_2 N(CF_3)_2$ or $R^F C(O)N(CF_3)_2$ where $R^F$=F or $C_p F_{2p+1}$, where p=1–8, are reacted with an alkali metal fluoride of the general formula DF, where D selected from the group of the alkali metals, in a polar organic solvent, and subsequently or simultaneously a salt of the general formula (4)

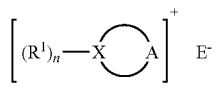

$$\left[ (R^1)_n - X \bigcirc A \right]^+ E^- \quad (4)$$

or a salt of the general formula (5)

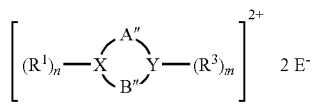

$$\left[ (R^1)_n - X \underset{B''}{\overset{A''}{\bigcirc}} Y - (R^3)_m \right]^{2+} 2 E^- \quad (5)$$

having a saturated, partially or fully unsaturated, heterocyclic 4- to 9-membered mono- or di-cation and an anion E⁻ selected from the group F⁻, Cl⁻, Br⁻, I⁻, $BF_4^-$, $ClO_4^-$, $AsF_6^-$, $SbF_6^-$, $SbCl_6^-$, $PF_6^-$, $R^F SO_3^-$, $FSO_3^-$, $(R^F)_2 P(O)O^-$, $R^F P(O)_2 O^-$, $RSO_3^-$, $ROSO_3^-$, $½SO_3^{2-}$, $CN^-$, $SCN^-$, $R^F C(O)O^-$, $RC(O)O^-$, 2,4-dinitrophenolate and 2,4,6-trinitrophenolate, where $R^F$=perfluorinated $C_1$ to $C_8$-alkyl group or perfluorinated aryl group and R=C, to $C_8$-alkyl group or aryl group, is added.

The heteroatoms X and Y, the parameters n and m, the hydrocarbon chains A, A" and B" and the substituents $R^1$, $R^2$ and $R^3$ of the salts of the general formula (4) or (5) are defined here as those in the general formulae (1) and (2).

In the reaction, fluoroalkylated sulfonic acid bis(trifluoromethyl)amide is preferably used for the reaction with the alkali metal fluoride.

In a variant which is preferred in accordance with the invention, the process is carried out as a one-pot reaction, i.e. the intermediate from alkali metal fluoride and fluoroalkylated sulfonic acid bis(trifluoromethyl)amide or acylbis(trifluoromethyl)-amide is not isolated, but instead reacted directly with the salt of the general formula (4) or (5). The reactants are preferably employed in approximately equimolar amount, with, on use of the acylbis(trifluoromethyl)amide, this being employed in twice the equimolar amount.

If the salt of the general formula (4) or (5) is employed in the form of its fluoride, i.e. if E⁻=F⁻, the reaction according to the invention can be carried out directly in a one-pot reaction and without added alkali metal fluoride DF.

It is possible for volatile by-products to form, which are then removed under reduced pressure. Usually, however, by-products form which are insoluble in the solvents used and are separated off by filtration. The solvent is, if desired, removed together with volatile by-products under reduced pressure. The salts according to the invention can generally be isolated with yields above 80%.

In order to improve the purity if too low, the salt according to the invention can be dissolved in a polar organic solvent and treated with rubidium imide $Rb^+ N(CF_3)_2^-$. The precipitating rubidium salt which forms is then filtered off, and the solvent is removed under reduced pressure.

The alkali metal fluoride used in accordance with the invention is preferably potassium or rubidium fluoride, particularly preferably the less expensive potassium fluoride.

The polar organic solvent which is preferred in accordance with the invention is selected from the group acetonitrile, dimethoxyethane, dimethylformamide and propionitrile.

The reaction according to the invention is preferably carried out at temperatures between −40° C. and 80° C., in particular between 0° C. and 40° C. and very particularly preferably at room temperature.

All compounds according to the invention have a salt-like character, relatively low melting points (usually below 100° C.) and can be used as ionic liquids.

The salts according to the invention can be employed as solvents for many synthetic or catalytic reactions, for example Friedel-Crafts acylation and alkylation, Diels-Alder cycloadditions, hydrogenation and oxidation reactions, Heck reactions. Furthermore, fluorinated solvents, for example, can be synthesised for secondary and primary batteries.

They are suitable as reagents for the introduction of $N(CF_3)_2$ groups. For example, $N(CF_3)_2$ groups can substitute the halogen atoms in organic halogen compounds. Furthermore, the salts according to the invention are of interest as precursors for the preparation of liquid-crystal compounds and of active ingredients, inter alia, for medicaments and crop-protection agents.

The use of the compounds according to the invention as non-aqueous electrolyte, if desired in combination with other electrolytes known to the person skilled in the art, is also possible.

In addition, the salts according to the invention can be used as non-aqueous, polar substances in suitable reactions as phase-transfer catalyst or as medium for the heterogenisation of homogeneous catalysts.

The complete disclosure content of all applications, patents and publications mentioned above and below is incorporated into this application by way of reference.

Even without further comments, it is assumed that a person skilled in the art will be able to utilise the above description in the broadest scope. The preferred embodiments and examples should therefore merely be regarded as descriptive disclosure which is absolutely not limiting in any way.

All NMR spectra were measured on a Bruker Avance 300 spectrometer ($^1$H: 300.13 MHz, $^{19}$F: 282.40 MHz).

EXAMPLE 1

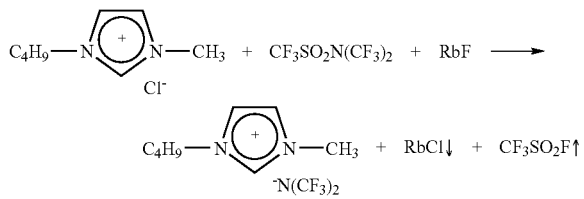

A solution of 2.93 g (12.3 mmol) of $Rb^+ N(CF_3)_2^-$, which was prepared from 1.29 g (12.3 mmol) of RbF and 3.63 g (12.7 mmol) of $CF_3SO_2N(CF_3)_2$ in 10 cm$^3$ of dry acetonitrile, is added at room temperature with stirring to a solution of 2.15 g (12.3 mmol) of 1-butyl-3-methylimidazolium chloride in 5 cm$^3$ of dry acetonitrile. The reaction mixture is stirred at room temperature for 15 min, and the precipitating RbCl is filtered off and washed with dry acetonitrile (2×5 cm$^3$). The acetonitrile is removed under a vacuum of 120 Pa, and the residue is dried for 2 hours at 50° C. under reduced pressure, giving 3.24 g of oil-like substances.

The yield of 1-butyl-3-methylimidazolium bis(trifluoromethyl)imide, $[C_8H_{15}N_2]^+ N(CF_3)_2^-$, is 90.5%.

$^{19}$F-NMR (reference: $CCl_3F$; solvent: $CD_3CN$): −37.35 s $^1$H-NMR (reference: TMS; solvent: $CD_3CN$): 0.93 t ($CH_3$); 1.32 m ($CH_2$); 1.83 m ($CH_2$); 3.87 s ($CH_3$); 4.17 t ($CH_2$); 7.46 dd (CH); 7.51 dd (CH); 9.08 br s (CH); $J^3_{H,H}$=7.3 Hz; $J^3_{H,H}$=7.4 Hz; $J_{H,H}$=1.8 Hz

EXAMPLE 2

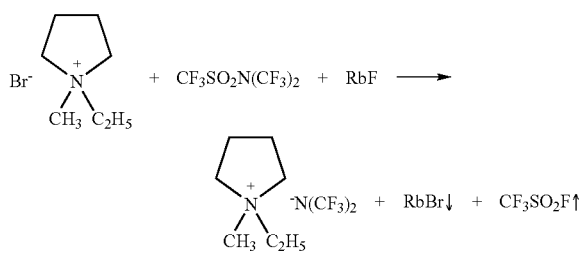

A solution of 4.65 g (19.6 mmol) of $Rb^+N(CF_3)_2^-$, which was prepared from 2.05 g (19.6 mmol) of RbF and 5.95 g (20.9 mmol) of $CF_3SO_2N(CF_3)_2$ in 20 cm$^3$ of dry acetonitrile, is added at room temperature with stirring to a solution of 3.65 g (18.8 mmol) of N-methyl-N-ethylpyrrolidinium bromide in 20 cm$^3$ of dry acetonitrile. The reaction mixture is stirred at room temperature for 15 min, and the precipitating RbBr is filtered off and washed with dry acetonitrile (2×5 cm$^3$). The acetonitrile is removed under a vacuum of 1.4 Pa, and the residue is dried for 2 hours at 60-65° C. under reduced pressure, giving 4.68 g of solid substances. The melting point is 80-85° C.

The yield of N-methyl-N-ethylpyrrolidinium bis(trifluoromethyl)imide, $[C_7H_{16}N]^+ N(CF_3)_2^-$, is 93.4%.

$^{19}$F-NMR (reference: $CCl_3F$; solvent: $CD_3CN$): −36.36 s $^1$H-NMR (reference: TMS; solvent: $CD_3CN$): 1.34 tm ($CH_3$); 2.17 m (2$CH_2$); 2.27 s ($CH_3$); 3.38 q ($CH_2$); 3.47 m (2$CH_2$); $J^3_{H,H}$=7.3 Hz

EXAMPLE 3

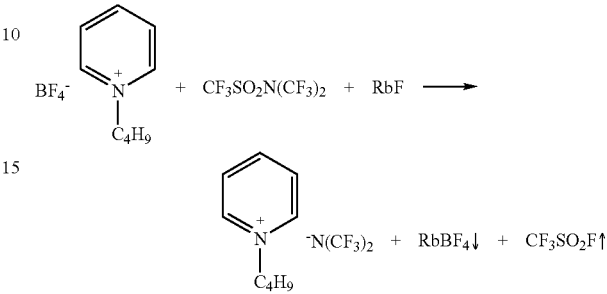

A solution of 6.93 g (29.2 mmol) of $Rb^+ N(CF_3)_2^-$, which was prepared from 2.05 g (29.2 mmol) of RbF and 8.43 g (29.6 mmol) of $CF_3SO_2N(CF_3)_2$ in 20 cm$^3$ of dry acetonitrile, is added at room temperature with stirring to a solution of 6.50 g (29.1 mmol) of N-butylpyridinium tetrafluoroborate in 15 cm$^3$ of dry acetonitrile. The reaction mixture is stirred at room temperature for 15 min, and the precipitating $RbBF_4$ is filtered off and washed with dry acetonitrile (2×5 cm$^3$). The acetonitrile is removed under a vacuum of 1.4 Pa, and the residue is dried for 2 hours at 60-65° C. under reduced pressure, giving 8.28 g of oil-like substances.

The yield of N-butylpyridinium bis(trifluoromethyl)imide, $[C_9H_{14}N]^+ N(CF_3)_2^-$, is 98.7%.

$^{19}$F-NMR (reference: $CCl_3F$; solvent: $CD_3CN$): −36.23 s $^1$H-NMR (reference: TMS; solvent: $CD_3CN$): 0.95 t ($CH_3$); 1.38 m ($CH_2$); 1.96 m ($CH_2$); 4.59 t ($CH_2$); 8.06 m (2CH); 8.54 tt (CH); 8.92 dm (2CH); $J^3_{H,H}$=7.3 Hz; $J^3_{H,H}$=7.5 Hz; $J_{H,H}$=7.9 Hz; $J_{H,H}$=1.3 Hz

EXAMPLE 4

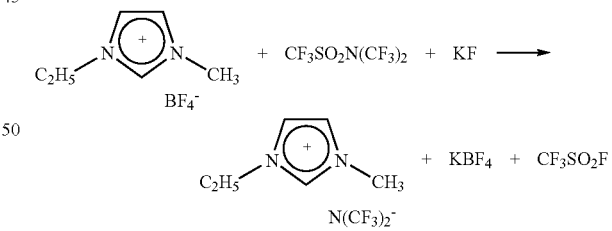

A solution of $K^+ N(CF_3)_2^-$, which was prepared from 1.90 g (32.7 mmol) of spray-dried potassium fluoride KF and 9.14 g (32.1 mmol) of $CF_3SO_2N(CF_3)_2$ in 25 cm$^3$ of dry dimethylformamide, is added at room temperature with stirring to a solution of 6.28 g (31.7 mmol) of 1-ethyl-3-methylimidazolium tetrafluoroborate in 10 cm$^3$ of dry dimethylformamide. The reaction mixture is stirred at room temperature for 15 min and subsequently cooled using an ice bath. The precipitating $KBF_4$ is filtered off and washed with dry dimethylformamide (10 cm$^3$). The solvent is removed at 30-35° C. under a vacuum of 1.3 Pa. The liquid is separated from the precipitate, giving 7.8 g of red-yellowish, oil-like substances.

The yield of 1-ethyl-3-methylimidazolium bis(trifluoromethyl)imide, $[C_6H_{11}N_2]^+ N(CF_3)_2^-$, is 93.5% with a purity (according to $^{19}$F-NMR measurement) of 86.5%.

In order to improve the purity, the salt is dissolved in 10 cm$^3$ of dry acetonitrile and treated with a solution of 1.35 g (5.7 mmol) of Rb$^+$ N(CF$_3$)$_2^-$ in 8 cm$^3$ of dry acetonitrile at room temperature. The precipitating RbBF$_4$ is filtered off and washed with dry acetonitrile (5 cm$^3$). The acetonitrile is removed at 30-35° C. under a vacuum of 1.3 Pa, giving 7.8 g of 1-ethyl-3-methylimidazolium bis(trifluoromethyl)imide, $[C_6H_{11}N_2]^+ N(CF_3)_2^-$, having a purity of 98%.

$^{19}$F-NMR (reference: CCl$_3$F; solvent: CD$_3$CN): −36.41 s $^1$H-NMR (reference: TMS; solvent: CD$_3$CN): 1.45 t (CH$_3$); 3.84 s (CH$_3$); 4.18 q (CH$_2$); 7.40 t (CH); 7.46 t (CH); 8.92 br. s (CH); $J^3_{H,H}$=7.3 Hz; $J_{H,H}$=1.8 Hz

EXAMPLE 5

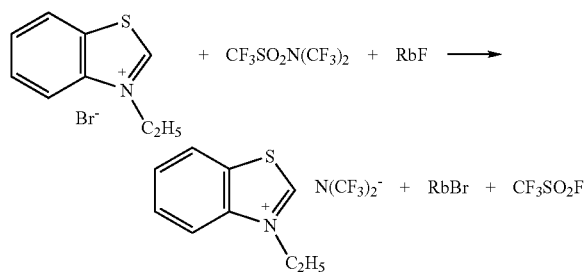

A solution of 0.69 g (2.9 mmol) of Rb$^+$ N(CF$_3$)$_2^-$, which was prepared from 0.303 g (2.9 mmol) of rubidium fluoride RbF and 0.83 g (2.9 mmol) of CF$_3$SO$_2$N(CF$_3$)$_2$ in 5 cm$^3$ of dry acetonitrile, is added at −35 to −38° C. with stirring to a solution of 0.71 g (2.9 mmol) of N-ethylbenzothiazolium bromide in 10 cm$^3$ of dry acetonitrile. The reaction mixture is stirred at −35 to −38° C. for 15 min, and the precipitated RbBr is subsequently filtered off at this temperature and washed with dry acetonitrile (2×5 cm$^3$). The residue are 0.48 g of rubidium bromide (positive sample with silver nitrate and no signals in the $^1$H and $^{19}$F NMR spectra). NMR-spectroscopic investigation of the acetonitrile solution at low temperature (−30° C.) showed the formation of N-ethylbenzothiazolium bis(trifluoromethyl)imide.

$^{19}$F-NMR (reference: CCl$_3$F; solvent: CD$_3$CN): −39.15 s.

The invention claimed is:

1. A salt of saturated, partially or fully unsaturated, heterocyclic cation having the bis(trifluoromethyl)imide anion, $N(CF_3)_2^-$, which have the general formula (1)

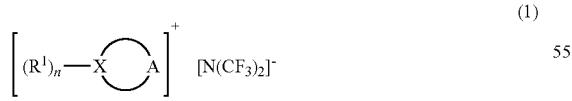

(1)

where

X=N, P, O or S n=an integer selected from 0, 1 or 2 wherein X is saturated in accordance with its valency increased by 1, A=a saturated, partially or fully unsaturated 3- to 8-membered hydrocarbon chain,
in which all carbon atoms apart from one may be replaced by identical or different heteroatoms selected from N, P, O and S,
where the carbon atoms of the hydrocarbon chain and the heteroatoms present therein are saturated by substituents R$^2$ in accordance with their valency, R$^1$, R$^2$=—H, with the proviso that there is no bond to the positively charged heteroatom,
straight-chain or branched alkyl having 1-20 carbon atoms
straight-chain or branched alkenyl having 2-20 carbon atoms and one or more double bonds,
straight-chain or branched alkynyl having 2-20 carbon atoms and one or more triple bonds,
saturated, partially or fully unsaturated cycloalkyl having 3-7 carbon atoms,
halogen, with the proviso that, for X=N, O, S, there is no halogen-heteroatom bond,
—NO$_2$, with the proviso that there is no bond to a positively charged heteroatom,
—CN, with the proviso that there is no bond to a positively charged heteroatom,
where the R$^2$ and/or R$^1$ in different and/or identical position of the heterocyclic ring are in each case identical or different,
where the R$^2$ and/or R$^1$ may be connected to one another in pairs by a single or double bond,
where one or more R$^2$ and/or R$^1$ may be partially or fully substituted by halogens, or partially by —CN or —NO$_2$, with the proviso that not all R$^2$ and R$^1$ are fully halogenated,
and where one or two carbon atoms of the R$^1$ and/or R$^2$ may be replaced by heteroatoms and/or atomic groups selected from the group —O—, —C(O)—, C(O)O—, —S—, —S(O)—, —SO$_2$—, —SO$_2$O—, —N=, —P=, —NH—, —PH—, —NR'— and —PR'— where R'= non-, partially or perfluorinated C$_1$- to C$_6$-alkyl or —C$_6$F$_5$, where the α-position of the R$^1$ is not replaced for X=O, S.

2. A salt according to claim 1, in which A is a 4-, 5- or 6-membered hydrocarbon chain.

3. A salt according to claim 1 in which A is a hydrocarbon chain in which zero, one or two carbon atoms are replaced by heteroatoms selected from N, P, O and S.

4. A salt according to claim 1, in which R$^1$, R$^2$, independently of one another, have the meaning —H, with the proviso that there is no bond to the positively charged heteroatom, halogen, with the proviso that for X=N, O, S, there is no halogen-heteroatom bond, straight-chain or branched alkyl having 1-6 carbon atoms, straight-chain or branched, partially or perfluorinated alkyl having 1-6 carbon atoms.

5. A salt according to claim 1, in which the saturated, partially or fully unsaturated, heterocyclic cation is selected from the following group:

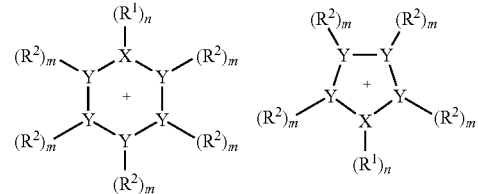

where

X=N, P, O or S

Y=in each case, independently of one another, N, P, O, S or C,
where at least one Y=C n=0 for unsaturated X=O, S 1 for saturated X=O, S or for unsaturated X=N, P 2 for saturated X=N, P m=0 for saturated Y=O, S or for unsaturated Y=N, P 1 for saturated Y=N, P or for Y=sp²-C
2 for Y=sp³-C
where the radicals R¹, R² are as defined in claim 1.

6. A salt according to claim 1, in which the saturated, partially or fully unsaturated, heterocyclic cation is selected from the following group:

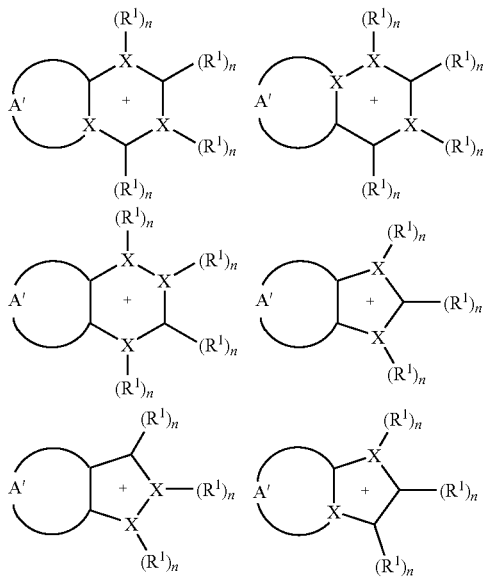

where
X=in each case, independently of one another, N, P, O, S or C, where at least one X=N, P, O or S
n=0 for saturated X=O, S or for unsaturated X=N, P
  1 for saturated X=N, P or for X=sp²-C or for substitution on the sp² ring carbon atom
  2 for X=sp³-C or for substitution on the sp³ ring carbon atom
  where n is increased by 1 for one X=N, P, O or S
A'=saturated, partially or fully unsaturated 2- to 7-membered hydrocarbon chain,
  where the carbon atoms of the hydrocarbon chain are saturated by substituents R² in accordance with their valency
where the radicals R¹, R² are as defined in claim 1, with the proviso that the substituents R¹ in the α-position to the positively charged heteroatom do not have a methylene group directly adjacent to the heterocyclic ring.

7. A salts according to claim 1, in which the saturated, partially or fully unsaturated, heterocyclic cation has the following structure

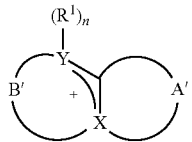

where
X=N or P
Y=N, P, O or S
n=0 for Y=O, S 1 for Y=N, P

A'=saturated, partially or fully unsaturated 2- to 7-membered hydrocarbon chain,
B'=saturated, partially or fully unsaturated 1- to 6-membered hydrocarbon chain,
where all carbon atoms of the hydrocarbon chains A' and B' apart from one may be replaced by identical or different heteroatoms selected from N, P, O and S and where the carbon atoms of the hydrocarbon chains A' and B' are saturated by substituents R² in accordance with their valency
and where the radicals R¹, R² are as defined in claim 1.

8. A salt of saturated, partially or fully unsaturated, heterocyclic di-cations having the bis(trifluoromethyl)imide anion, $N(CF_3)_2^-$, which have the formula (2)

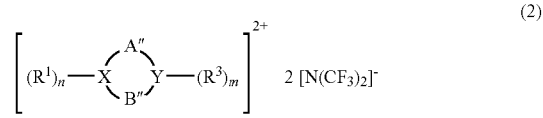

(2)

where
X, Y=each, independently of one another, N, P, O or S
n, m=an integer selected from 0, 1 or 2 in such a way that X and Y are each saturated in accordance with their valency increased by 1,
A'', B''=saturated, partially or fully unsaturated 0- to 4-membered hydrocarbon chain,
  in which the carbon atoms may be replaced by identical or different heteroatoms selected from N, P, O and S,
  where at least one carbon atom is present in the chains A'' and B'' together and
  where the carbon atoms of the hydrocarbon chains A'' and B'' and the heteroatoms present therein are saturated by substituents R² in accordance with their valency,
R¹, R², R³=—H, with the proviso that there is no bond to the positively charged heteroatom,
  straight-chain or branched alkyl having 1-20 carbon atoms,
  straight-chain or branched alkenyl having 2-20 carbon atoms and one or more double bonds,
  straight-chain or branched alkynyl having 2-20 carbon atoms and one or more triple bonds,
  saturated, partially or fully unsaturated cycloalkyl having 3-7 carbon atoms,
  halogen, with the proviso that, for X, =N, O, S, there is no halogen-heteroatom bond,
  —NO₂, with the proviso that there is no bond to a positively charged heteroatom,
  —CN, with the proviso that there is no bond to a positively charged heteroatom,
  where the R¹, R² and/or R³ in different and/or identical position of the heterocyclic ring are in each case identical or different,
  where the R¹, R² and/or R³ may be connected to one another in pairs by a single or double bond,
  where one or more R¹, R² and/or R³ may be partially or fully substituted by halogens, in particular or partially by —CN or —NO₂, with the proviso that that not all R¹, R² and R³ are fully halogenated,
  and where one or two carbon atoms of the R¹, R² and/or R³ may be replaced by heteroatoms and/or atomic groups selected from the group —O—, —C(O)—, C(O)O—, —S—, —S(O)—, —SO₂—, —SO₂O—, —N=, —P=, —NH—, —PH—, —NR'— and —PR'— where R'=non-, partially or perfluorinated C₁- to C₆-alkyl or —$C_6F_5$, where the α-positions of the $R^1$ and of the $R^3$ are not replaced for X=O, S or Y=O, S, where the heterocyclic di-cation is a 4-, 5-, 6-, 7-, 8- or 9-membered ring.

9. A salt according to claim 8, in which the heterocyclic di-cation is a 5-, 6- or 7-membered ring.

10. A salt of saturated, partially or fully unsaturated, heterocyclic cations having the bis(trifluoromethyl)imide anion, $N(CF_3)_2^-$, which have the formula (3)

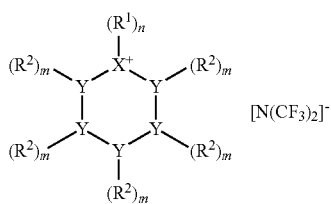

(3)

[$N(CF_3)_2$]⁻ where

X, Y=each, independently of one another, N, P, O or S n=an integer selected from 0, 1 or 2 in such a way that X is saturated in accordance with its valency increased by 1, m=an integer selected from 0, 1 or 2 in such a way that Y is saturated in accordance with its valency, $R^1$, $R^2$=—H, with the proviso that there is no bond to the positively charged hetero-atom, straight-chain or branched alkyl having 1-20 carbon atoms straight-chain or branched alkenyl having 2-20 carbon atoms and one or more double bonds straight-chain or branched alkynyl having 2-20 carbon atoms and one or more triple bonds saturated, partially or fully unsaturated cycloalkyl having 3-7 carbon atoms, halogen, with the proviso that, for X, =N, O, S, there is no halogen-heteroatom bond, —OR, with the proviso that the substituted heteroatom is not O or S, where the $R^2$ and/or $R^1$ in different and/or identical position of the heterocyclic ring are in each case identical or different, where the $R^2$ and/or $R^1$ may be connected to one another in pairs by a single or double bond, where one or more $R^2$ and/or $R^1$ may be partially or fully substituted by a halogens, or partially by —CN or —$NO_2$, with the proviso that not all $R^2$ and $R^1$ are fully halogenated, and where one or two carbon atoms of the $R^1$ and/or $R^2$ may be replaced by heteroatoms and/or atomic groups selected from the group —O—, —C(O)—, C(O)O—, —S—, —S(O)—, —$SO_2$—, —$SO_2$O—, —N=, —P=, —NH—, —PH—, —NR'— and —PR'— where R'=non-, partially or perfluorinated $C_1$- to $C_6$-alkyl or —$C_6F_5$, where the α-position of the $R^1$ is not replaced for X=O, S.

11. A salt according to claim 1, where one or more $R^2$ and/or $R^1$ may be partially or fully substituted by —F and/or —Cl.

12. A salt according to claim 4, in which $R^1$ or $R^2$ are —$CH_3$, —$C_2H_5$, -n-$C_3H_7$, —$CH(CH_3)_2$, -n-$C_4H_9$, -n-$C_6H_{13}$, —$CF_3$, —$C_2F_5$, or —$C_4F_9$.

13. A salt according to claim 1, which is at least partially miscible in water.

14. A process for the preparation of salts according to claim 1, wherein an alkali metal fluoride of the general formula DF, where D selected from the group of the alkali metals, is reacted in a polar organic solvent with $R^FSO_2N(CF_3)_2$ or $R^FC(O)N(CF_3)_2$ where $R^F$=F or $C_pF_{2p+1}$, where p=1-8, and a salt of the general formula (4)

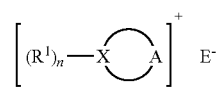

(4)

where $E^-$=$F^-$, $Cl^-$, $Br^-$, $I^-$, $BF_4^-$, $ClO_4^-$, $AsF_6^-$, $SbF_6^-$, $SbCl_6^-$, $PF_6^-$, $R^FSO_3^-$, $FSO_3^-$, $(R^F)_2P(O)O^-$, $R^FP(O)_2O^-$, $RSO_3^-$, $ROSO_3^-$, $1/2SO_3^{2-}$, $CN^-$, $SCN^-$, $R^FC(O)O^-$, $RC(O)O^-$, 2,4-dinitrophenolate or 2,4,6-trinitrophenolate, where $R^F$ is a perfluorinated $C_1$ to $C_8$-alkyl group or perfluorinated aryl group and R is a $C_1$ to $C_8$-alkyl group or aryl group X=N, P, O or S n=an integer selected from 0, 1 or 2 in such a way that X is saturated in accordance with its valency increased by 1, A=a saturated, partially or fully unsaturated 3- to 8-membered hydrocarbon chain, in which all carbon atoms apart from one may be replaced by identical or different heteroatoms selected from N, P, O and S, where the carbon atoms of the hydrocarbon chain and the heteroatoms present therein are saturated by substituents $R^2$ in accordance with their valency, $R^1$, $R^2$=—H, with the proviso that there is no bond to the positively charged heteroatom, straight-chain or branched alkyl having 1-20 carbon atoms straight-chain or branched alkenyl having 2-20 carbon atoms and one or more double bonds straight-chain or branched alkynyl having 2-20 carbon atoms and one or more triple bonds saturated, partially or fully unsaturated cycloalkyl having 3-7 carbon atoms halogen, with the proviso that, for X=N, O, S, there is no halogen-heteroatom bond, —$NO_2$, with the proviso that there is no bond to a positively charged heteroatom, —CN, with the proviso that there is no bond to a positively charged heteroatom, where the $R^2$ and/or $R^1$ in different and/or identical position of the heterocyclic ring are in each case identical or different, where the $R^2$ and/or $R^1$ may be connected to one another in pairs by a single or double bond, where one or more $R^2$ and/or $R^1$ may be partially or fully substituted by a halogen —Cn, —CN or —$NO_2$, with the proviso that not all $R^2$ and $R^1$ are fully halogenated, and where one or two carbon atoms of the $R^1$ and/or $R^2$ may be replaced by heteroatoms and/or atomic groups selected from the group —O—, —C(O)—, C(O)O—, —S—, —S(O)—, —$SO_2$—, —$SO_2$O—, —N=, —P=, —NH—, —PH—, —NR'— and —PR'— where R'=non-, partially or perfluorinated $C_1$- to $C_6$-alkyl or —$C_6F_5$, where the α-position of the $R^1$ is not replaced for X=O, S.

15. A process for the preparation of salts according to claim 8, wherein an alkali metal fluoride of the formula DF, where D selected from the group of the alkali metals, is reacted in a polar organic solvent with

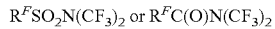

where $R^F$=F or $C_pF_{2p+1}$, where p=1-8, and a salt of the general formula (5)

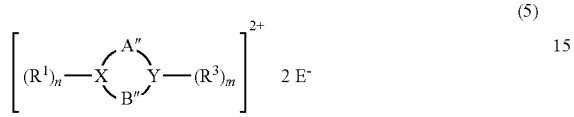

where
$E^-$=$F^-$, $Cl^-$, $Br^-$, $I^-$, $BF_4^-$, $ClO_4^-$, $AsF_6^-$, $SbF_6^-$, $SbCl_6^-$, $PF_6^-$, $R^FSO_3^-$, $FSO_3^-$, $(R^F)_2P(O)O^-$, $R^FP(O)_2O^-$, $RSO_3^-$, $ROSO_3^-$, $1/2SO_3^{2-}$, $CN^-$, $SCN^-$, $R^FC(O)O^-$, $RC(O)O^-$, 2,4-dinitrophenolate or 2,4,6-trinitrophenolate, where $R^F$ is a perfluorinated $C_1$ to $C_8$-alkyl group or perfluorinated aryl group and R is a $C_1$ to $C_8$-alkyl group or aryl group X, Y=each, independently of one another, N, P, O or S n, m=an integer selected from 0, 1 or 2 in such a way that X, Y are each saturated in accordance with their valency increased by 1, A", B"=saturated, partially or fully unsaturated 0- to 4-membered hydrocarbon chain,
in which the carbon atoms may be replaced by identical or different heteroatoms selected from N, P, O and S,
where at least one carbon atom is present in the chains A" and B" together and
where the carbon atoms of the hydrocarbon chains A" and B" and the heteroatoms present therein are saturated by substituents $R^2$ in accordance with their valency, $R^1$, $R^2$, $R^3$=—H, with the proviso that there is no bond to the positively charged heteroatom,
straight-chain or branched alkyl having 1-20 carbon atoms
straight-chain or branched alkenyl having 2-20 carbon atoms and one or more double bonds
straight-chain or branched alkynyl having 2-20 carbon atoms and one or more triple bonds
saturated, partially or fully unsaturated cycloalkyl having 3-7 carbon atoms
halogen, in particular fluorine or chlorine, with the proviso that, for X, =N, O, S, there is no halogen-heteroatom bond,
halogen, with the proviso that there is no halogen-heteroatom bond,
—$NO_2$, with the proviso that there is no bond to a positively charged heteroatom,
—CN, with the proviso that there is no bond to a positively charged heteroatom,
where the $R^1$, $R^2$ and/or $R^3$ in different and/or identical position of the heterocyclic ring are in each case identical or different,
where the $R^1$, $R^2$ and/or $R^3$ may be connected to one another in pairs by a single or double bond,
where one or more $R^1$, $R^2$ and/or $R^3$ may be partially or fully substituted by halogens, in particular —F and/or —Cl, or partially by —CN or —$NO_2$, with the proviso that not all $R^1$, $R^2$ and $R^3$ are fully halogenated,
and where one or two carbon atoms of the $R^1$, $R^2$ and/or $R^3$ may be replaced by heteroatoms and/or atomic groups selected from the group —O—, —C(O)—, C(O)O—, —S—, —S(O)—, —$SO_2$—, —$SO_2$O—, —N=, —P=, —NH—, —PH—, —NR'— and —PR'— where R'=non-, partially or perfluorinated $C_1$- to $C_6$-alkyl or —$C_6F_5$, where the α-position of the $R^1$ is not replaced for X=O, S, where the heterocyclic di-cation is a 4-, 5-, 6-, 7-, 8- or 9-membered ring.

16. Process according to claim 14, wherein the alkali metal fluoride employed is KF or RbF.

17. A process according to claim 14, wherein the reaction takes place at temperatures between −40° C. and 80° C.

18. A process according to claim 14, wherein the reaction takes place in a polar organic solvent selected from the group acetonitrile, dimethoxyethane, dimethylformamide and propionitrile.

19. A process according to claim 14, wherein the reaction is carried out as a one-pot reaction.

20. A process according to claim 14, wherein the the reaction for $E^-$=$F^-$ is carried out without added alkali metal fluoride DF.

21. A process according to claim 14, wherein the starting materials for the reaction are employed in approximately equimolar ratio to one another.

22. A process according to claim 17, wherein the reaction takes place at temperatures between 0° C. to 40° C.

23. An ionic liquid comprising a salt according to claim 1.

24. A non-aqueous electrolyte comprising a salt according to claim 1.

25. A reagent for the introduction of $N(CF_3)_2$ groups comprising a salt according to claim 1.

26. A phase-transfer catalyst comprising a salt according to claim 1.

27. An intermediate for the synthesis of liquid-crystal compounds or active ingredients comprising a salt according to claim 1.

28. A medicament or crop-protection agent comprising a salt according to claim.

* * * * *

UNITED STATES PATENT AND TRADEMARK OFFICE
CERTIFICATE OF CORRECTION

| | | |
|---|---|---|
| PATENT NO. | : 7,550,491 B2 | Page 1 of 1 |
| APPLICATION NO. | : 10/538847 | |
| DATED | : June 23, 2009 | |
| INVENTOR(S) | : Ignatyev et al. | |

It is certified that error appears in the above-identified patent and that said Letters Patent is hereby corrected as shown below:

Column 17, line 49 reads, "A salt of saturated, partially or fully unsaturated, hetero-" should read -- A salt of a saturated, partially or fully unsaturated, hetero- --

Column 17, line 51 reads "$N(CF_3)_2$-, which have the general formula (1)" should read -- $N(CF_3)_2$-, which have the formula (1) --

Column 19, line 52 reads "7. A salts according to claim 1, in which the saturated," should read -- A salt according to claim 1, in which the saturated, --

Column 20, line 59 reads "fully substituted by halogens, in particular or partially" should read -- fully substituted by halogen, or partially --

Column 21, line 48 reads "substituted by a halogens, or partially by -CN or" should read -- substituted by a halogen, or partially by -CN or --

Column 22, line 2 reads "1, wherein an alkali metal fluoride of the general formula DF," should read -- wherein an alkali metal fluoride of the formula DF, --

Column 22, line 7 reads "and a salt of the general formula (4)" should read -- and a salt of the formula (4) --

Column 22, line 60 reads "substituted by a halogen -Cn, -CN or -$NO_2$, with" should read -- substituted by a halogen -C1, -CN or -$NO_2$, with --

Column 22, line 54 reads "salt according to claim." should read -- salt according to claim 1 --

Signed and Sealed this
Eighth Day of February, 2011

David J. Kappos
*Director of the United States Patent and Trademark Office*